United States Patent [19]
Akhavi et al.

[11] Patent Number: 5,593,438
[45] Date of Patent: Jan. 14, 1997

[54] INTRAOCULAR LENS WITH METALLIC COATINGS FOR PREVENTING SECONDARY CATARACTS

[76] Inventors: David S. Akhavi; Damian A. C. Akhavi, both of 10966 Roebling Ave. #6A, Los Angeles, Calif. 90024

[21] Appl. No.: 375,819

[22] Filed: Jan. 20, 1995

[51] Int. Cl.⁶ .................................................. A61F 2/16
[52] U.S. Cl. ................... 623/6; 623/4; 604/265; 606/76; 607/75; 607/76
[58] Field of Search ............. 623/4, 6; 604/265, 604/266; 606/76; 607/75, 76

[56] References Cited

U.S. PATENT DOCUMENTS

| | | | |
|---|---|---|---|
| 4,612,012 | 9/1986 | White | 623/5 |
| 4,615,705 | 10/1986 | Scales et al. | 623/11 |
| 4,886,505 | 12/1989 | Haynes et al. | 604/265 |
| 5,295,979 | 3/1994 | DeLaurentis et al. | 604/265 |
| 5,326,567 | 7/1994 | Capelli | 424/405 |
| 5,370,687 | 12/1994 | Poler | 623/6 |

*Primary Examiner*—Paul B. Prebilic

[57] ABSTRACT

An intraocular lens (IOL) with an oligodynamic metallic coating on its peripheral portion to substantially inhibit the migration of microorganisms towards the optical axis of the lens, where said coating is either an oligodynamic metal, or the combination of an oligodynamic metal and one or more noble metals which are more electronegative than said oligodynamic metal for substantially reducing the formation of secondary cataracts in the central posterior region of the optic in the capsular bag.

7 Claims, 3 Drawing Sheets

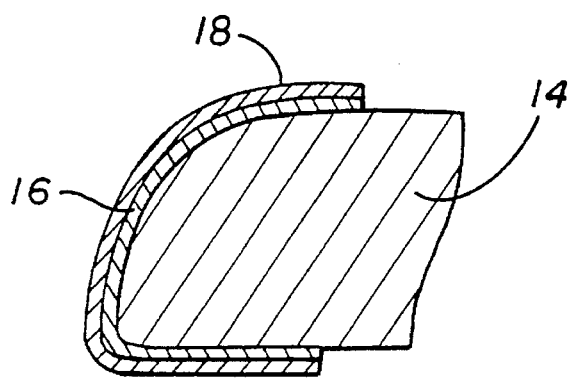
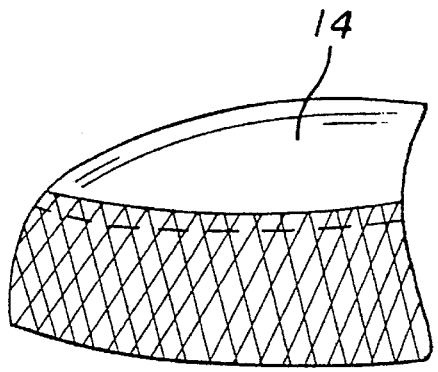
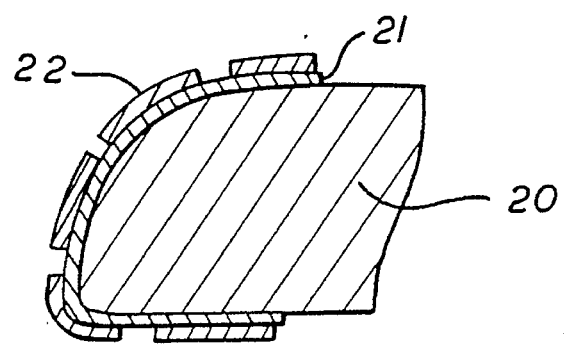

INTRAOCULAR LENS WITH METALLIC COATINGS FOR PREVENTING SECONDARY CATARACTS

BACKGROUND OF THE INVENTION

One of the major complications that often arises after extracapsular cataract extraction (ECCE) and intraocular lens (IOL) implantation, is post operative opacification. Opacification is caused by the proliferation of lens epithelial cells and other remnants. It has been suggested that some residual cortex left in the periphery of the capsular bag over time, proliferate to the central portion of the posterior portion of the bag, resulting in decreased transparency and visual acuity at the optical axis. The result of postoperative opacification requires the use of a YAG laser or secondary cataract surgery to remove the posterior portion of the bag, but not without their side effects. Complications arising from the use of a YAG laser may include: damage to the IOL, a transient rise in intraocular pressure, cystoid macular edema, and retinal detachment.

Several solutions have been proposed in prior literature and patents for preventing postoperative opacification. Proposed solutions vary from alterations in the IOL design for means of mechanical inhibition, variations in surgical procedures and the administration of different drugs. In view of the statistics of the relatively high percentage of reoccurring opacification, no adequate solution exists at the present time that minimizes the necessity for cataract patients with IOL implants to require secondary cataract surgery. It is therefore the primary object of the present invention, to inhibit the migration and or growth of microorganisms toward the visual axis of the IOL implant.

SUMMARY OF THE INVENTION

The present invention provides the substantial inhibition of microorganisms from migrating toward the optical portion of an IOL. The migration of deleterious microorganisms is inhibited by coating the periphery of the IOL optic with an oligodynamic metal, such as silver. Silver in various forms has a long history in medicine as a means of inhibiting gram positive, gram negative, aerobic and anaerobic microorganisms. A greater zone of inhibition in the immediate area surrounding the lens can be achieved by having the metallic coating composed of dissimilar metals, where one metal is an oligodynamic metal, and the other a more electronegative (noble) metal than said oligodynamic metal. The combination of an oligodynamic metal such as silver, and a more noble metal such as platinum can result in the formation of an iontophoretic (ion-pumping) galvanic couple, releasing ions into the surrounding fluid. The fluid of the eye acts as an electrolyte, in which the minute electrical charges created by said dissimilar metals can be carried, resulting in an inhibition zone surrounding the optic portion of the lens.

BRIEF DESCRIPTION OF THE DRAWINGS

FIG. 3A is a fractional cross sectional view of a fragmented edge of an embodiment of an IOL herein where the oligodynamic metallic coating is composed of two dissimilar, continuous layers, where one is an oligodynamic metal, and the other, a more electronegative (noble) metal which coating extends from a portion of the anterior side (as shown in FIG. 1), down the side of the IOL and over a portion of the posterior side of said IOL.

FIG. 3B is a fractional side view of the embodiment shown in FIG. 3A, where the oligodynamic material can be applied on top of a base metal, where the base metal can be a dissimilar metal (more noble) for the purpose of forming an iontophoretic galvanic couple, or the base metal can serve as the top layer, while the oligodynamic metal is the underlying layer.

FIG. 4A is a fractional cross sectional view of still another embodiment of an IOL herein wherein the antimicrobial coating is comprised of two dissimilar metals, where one is an oligodynamic metal, and the other a more noble metal, where one metal is applied in a continuous layer, and the other in a discontinuous layer to result in both dissimilar metals being exposed.

DETAILED DESCRIPTION OF THE INVENTION

The invention herein is directed to an improved intraocular lens (IOL) and will be described in regard to the accompanying drawings which illustrate the invention in differing embodiment of an Intraocular Lens (IOL) 10 of the invention herein having an oligodynamic metallic coating 12 on the peripheral portion of the IOL 10. The oligodynamic coating can be any suitable oligodynamic metal compatible within the human eye. The coating 12 can extend from a portion of the anterior side, across the annular edge or side of the IOL, and along a portion of the posterior surface as well.

Figure 1:
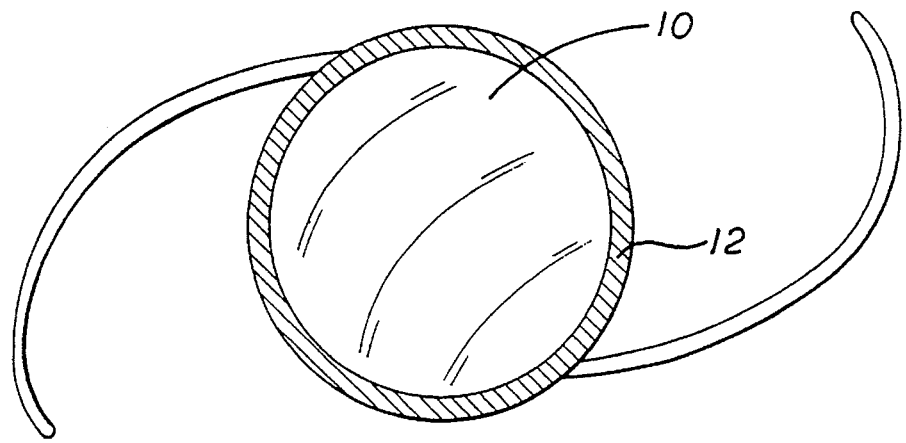
FIG. 1 is an Anterior view of an Intraocular Lens (IOL) of the invention herein illustrating the oligodynamic metallic coating on the peripheral portion of the IOL optic. The coating can extend from the anterior side, down the side of the optic, and along the posterior surface as well.
Figure 2A:
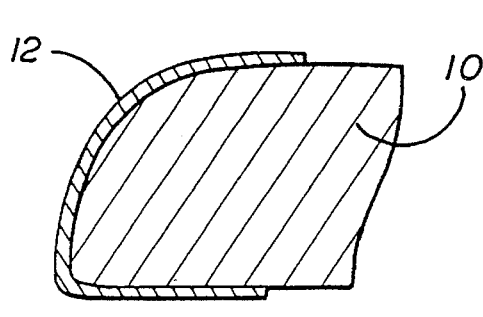
FIG. 2A is a fractional cross sectional view of a fragmented edge of an embodiment of an IOL herein where the oligodynamic metallic coating extends from a portion of the anterior side (as shown in FIG. 1), down the side of the IOL and over a portion of the posterior side of said IOL.

FIG. 2A is a fractional cross sectional view of a fragmented edge of the embodiment illustrated in FIG. 1 further illustrating the IOL 10 therein where the oligodynamic metallic metallic coating 12 extends from a portion of the anterior side (as shown in FIG. 1), across the annular edge of the IOL and over a portion of the posterior side of the IOL.

Figure 2B:
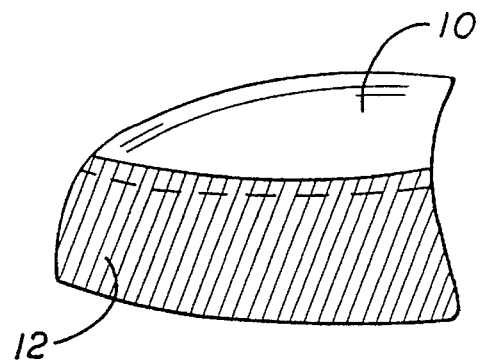
FIG. 2B is a fractional side view of an embodiment of an IOL herein illustrating an oligodynamic metallic coating, on the peripheral portion of the IOL.

FIG. 2B also shows the IOL 10 in a fractional side view illustrating the oligodynamic coating 12 on the peripheral annular edge of the IOL 10.

FIG. 3A is a fractional cross sectional view of a fragmented edge of an embodiment of an IOL 14 herein where an oligodynamic metallic coating is composed of two dissimilar, continuous layers. The first layer 16 is an oligodynamic metal such as the coating 12 described above with respect to the embodiment of FIG. 1. The second layer 18 is a more electronegative (noble) metal which coating extends from a portion of the anterior side, across the annular edge of the IOL 14 and over a portion of the posterior side of the IOL. FIG. 3B is a fractional side view of the embodiment shown in FIG. 3A, showing how the coating can extend from covering a portion of the anterior surface, across the annular edge and over a portion of the posterior surface of the IOL. While this embodiment has been described initially with the oligodynamic coating being the first layer 16 and the noble metal comprising the second layer 18, the composition of the layers can be switched such that the oligodynamic metal can be the outer layer and applied on top of a base metal, where the base metal can be a dissimilar metal (more noble) for the purpose of forming an iontophoretic galvanic couple.

FIG. 4A is a fractional cross sectional view of still another embodiment of an IOL 20 herein wherein the antimicrobial coating is comprised of two dissimilar metals, wherein a first metal coating 21 is an oligodynamic metal, and the second metal coating 22 is a more noble metal. In this embodiment the first metal coating 21 is applied in a continuous layer, and the second metal coating 22 is applied in a discontinuous layer to result in both metals being exposed.

Figure 4B:
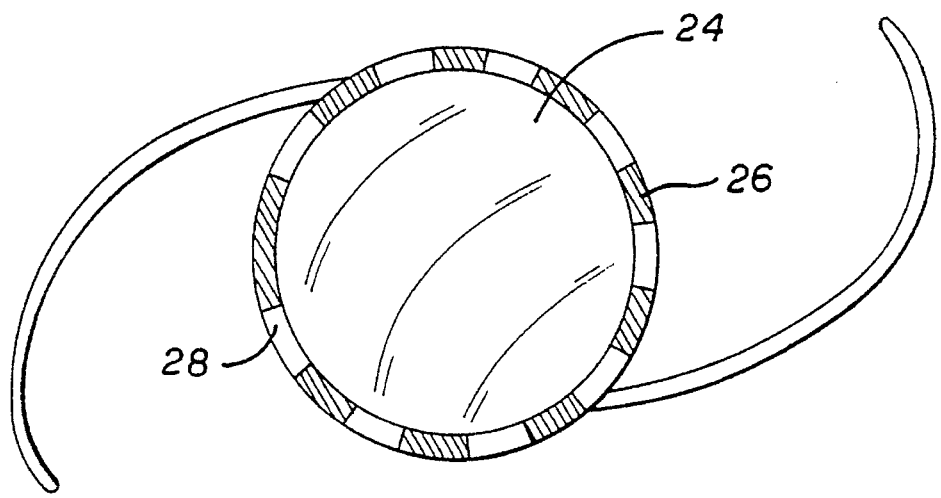
FIG. 4B is a top view of still another embodiment of an IOL showing two dissimilar metals, both exposed as a result of the base layer being continually deposited, and the second layer discontinuously deposited, where one of the dissimilar metals is an oligodynamic metal, and the other a more electronegative (noble) metal.
Figure 4C:
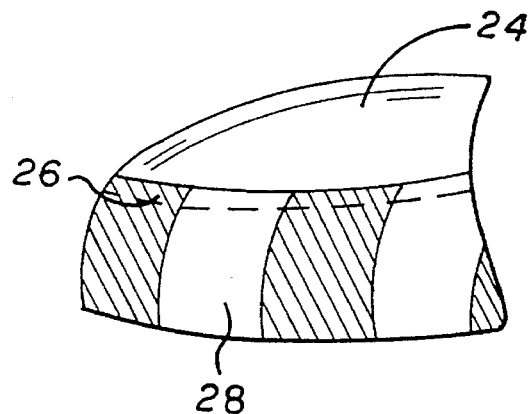
FIG. 4C is a fractional side view of the cross section in FIG. 4B.

FIG. 4B is a top view of still another embodiment of an IOL 24 showing two dissimilar metals deposited on the IOL and providing the antimicrobial coating in a similar manner to the embodiment in FIG. 4A. FIG. 4C is a fractional view of the same embodiment as FIG. 4B. In FIGS. 4B and 4C, the IOL 24 has an antimicrobial coating comprised of a first coating 26 of an oligodynamic metal and a second metal coating 28 which is a more electronegative (noble) metal partially deposited over the first coating 26 such that both metal coatings are exposed as a result of the first coating 26 (base layer) being continuously deposited, and the second coating 28 discontinuously deposited. The metal composition of the two coatings can be switched such that the oligodynamic metal can be the outer coating 28 and applied on top of a more noble metal coating 26, for the purpose of forming an iontophoretic galvanic couple.

Figure 5:
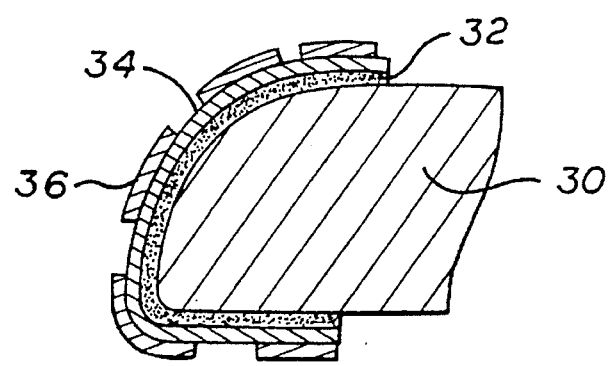
FIG. 5 is a fractional cross sectional view of one of the variations of combinations of deposition, such that an oligodynamic metal desired has bad adhesive characteristics to the IOL optic material.

FIG. 5 is a fractional cross sectional view of still another embodiment of the invention herein. This embodiment illustrates one of the variations of combinations of deposition of the metal coatings. In this embodiment an IOL 30 is first coated with a metal coating 32 which has good adhesive properties for the IOL. An oligodynamic metal layer 34 can then be coated on to the adhesive layer 32. This deposition technique can be useful when the oligodynamic coating does not have a sufficient adhesivity for the material of the IOL. The more noble metal coating 36 can optionally be deposited over the oligodynamic metal coating 34 in a manner such as described with regard to FIG. 4B, such as to form a discontinuous coating. The base metal can first be applied to form the layer 34 over which the oligodynamic metal can be deposited to form layer 36 if desired.

The term oligodynamic refers to a material that is effective as an antimicrobial in extremely small quantities. Several theories have been offered with regards to the exact mechanisms involved in the oligodynamic phenomenon, that causes microbial inhibition. An excellent treatment of the topic can be found in Chapters 24 and 28 of "Disinfection, Sterilization and Prevention" by Lawrence and Black; (Lea and Fibiger, Philadelphia, 1968). The antimicrobial metallic coating around the peripheral edge of the optic portion of the IOL can extend from a portion of the anterior side of the lens, across the annular edge of the optic and over a posterior portion as well (forming a circumferential metallic coating around the IOL). The metallic coatings can be deposited by any of the following methods many techniques for metallic deposition are well known by the skilled artisan and such techniques are not meant to limit the invention herein: sputtering, evaporation, electrodeposition, ion beam implantation, and the like.

In the event the metallic coating is composed of only the oligodynamic metal, it can be applied so as to be mobile or immobile, that is it can be embedded within the plastic, where the surface of the oligodynamic metal is exposed, proving effective as a contact agent only, or it can be deposited on the surface of the lens, where it can be easily ionized. To prevent the rapid dislocation of the oligodynamic metal from the lens surface, a base metal can be used. In this combination, the base metal would have good adhesive characteristics to whatever material the IOL optic is composed. The base metal, can be a more noble metal than said oligodynamic metal.

When the metallic coating is composed of dissimilar metals, the application of such metals can vary. As stated herein the oligodynamic metallic layer can be the base layer, and a more noble metal can be deposited as the second metallic layer. As described above alternatively, a more noble metal can be applied as the first layer, and an oligodynamic metal can be applied as the second layer. The invention herein contemplates the flexibility to apply the oligodynamic coating in multiple coatings, where the base layer is a continuous layer, and the second layer is deposited in a discontinuous manner to result in both metals being exposed. In the case of two dissimilar metals being used, they are positioned to provide physical and electrical contact. The best methods of combining dissimilar metals, and the efficacy of one oligodynamic and noble metal to another for this particular application to the human eye is within the skill of a skilled artisan. Those skilled in the art, will realize the flexibility available in depositing the metallic coatings on the peripheral portion of the IOL.

In accordance with an aspect of this invention, the second more noble metal such as platinum when the oligodynamic metal is silver. By partially exposing both metals a galvanic couple is created which promotes iontophoresis, or the generation of ions, the generation of silver ions. The silver ions go into solution at a sufficient density to provide microbial inhibition. Among the metals useful herein is silver. Gold is another oligodynamic metal which can also be useful in the invention herein.

An intraocular lens (IOL) is formed which has a metallic oligodynamic coating on its peripheral portion to substantially inhibit the migration of microorganisms towards the optical axis of the lens, which coating is either an oligodynamic metal, or the combination of an oligodynamic metal and a dissimilar metal, one more noble than the oligodynamic metal. This invention provides the benefit of substantially reducing the formation of secondary cataracts in the central posterior region of the optic in the capsular bag.

We claim:

1. In a transparent intraocular lens having an anterior surface and a posterior surface joined by an annular edge, the improvement comprising an oligodynamic metal coating and a more electronegative metal coating in direct contact with the oligodynamic metal coating extending across the annular edge.

2. An intraocular lens as recited in claim 1 wherein the oligodynamic metal coating extends over a portion of the anterior surface and a portion of the posterior surface.

3. An intraocular lens as recited in claim 1 wherein the more noble metal second coating is deposited in a discontinuous pattern.

4. An intraocular lens as recited in claim 1 wherein the oligodynamic metal is embedded in the peripheral portion of the lens.

5. An intraocular lens as recited in claim 1 wherein the oligodynamic metal comprises silver or complexes of silver which are compatible within the ocular environment.

6. An intraocular lens as recited in claim 1 wherein the oligodynamic metal comprises gold or complexes of gold which are compatible within the ocular environment.

7. An intraocular lens as recited in claim 1 wherein the oligodynamic metal comprises noble metals, heavy metals, or complexes of said metals that are compatible within the ocular environment.

* * * * *